United States Patent
Metzger et al.

(10) Patent No.: US 6,365,737 B1
(45) Date of Patent: Apr. 2, 2002

(54) PROCESS FOR THE PREPARATION OF STILBENE COMPOUNDS

(75) Inventors: Georges Metzger, Moernach; Fabienne Cuesta, Roppentzwiller, both of (FR); Peter Rohringer, Schönenbuch (CH); Dieter Reinehr, Kandern (DE); René Schlatter, Basel (CH)

(73) Assignee: Ciba Specialty Chemical Corporation, Tarrytown, NY (US)

( * ) Notice: Subject to any disclaimer, the term of this patent is extended or adjusted under 35 U.S.C. 154(b) by 0 days.

(21) Appl. No.: 09/622,472

(22) PCT Filed: Feb. 13, 1999

(86) PCT No.: PCT/EP99/00950

§ 371 Date: Aug. 17, 2000

§ 102(e) Date: Aug. 17, 2000

(87) PCT Pub. No.: WO99/42454

PCT Pub. Date: Aug. 26, 1999

(30) Foreign Application Priority Data

Feb. 20, 1998 (EP) .............................. 98810140

(51) Int. Cl.[7] .............................. C07D 251/68
(52) U.S. Cl. .................... 544/193.2; 544/113
(58) Field of Search .............. 544/193.2, 113

(56) References Cited

U.S. PATENT DOCUMENTS

| | | | |
|---|---|---|---|
| 4,737,240 A | 4/1988 | Davis et al. ............... | 162/162 |
| 5,288,294 A | 2/1994 | Käser ........................ | 8/687 |

FOREIGN PATENT DOCUMENTS

| | | |
|---|---|---|
| DE | 19500791 | 8/1996 |
| EP | 0728749 | 8/1996 |
| FR | 2611365 | 9/1988 |
| GB | 2203426 | 10/1988 |
| GB | 2293381 | 3/1996 |

OTHER PUBLICATIONS

Organic Chemistry, D. J. Cram and G. S. Hammond, Second Edition, McGraw–Hill Book Company Inc., pp. 52–57.

Primary Examiner—Richard L. Raymond
Assistant Examiner—Venkataraman Balasubramanian
(74) Attorney, Agent, or Firm—Kevin T. Mansfield

(57) ABSTRACT

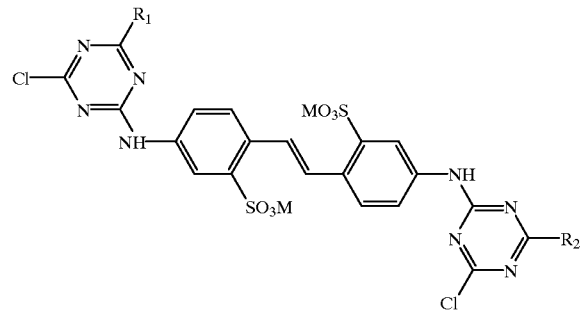

A process for the preparation of a 4,4'-bis-(triazinylamino)-stilbene-2,2'-disulphonic acid compound of formula (1) is disclosed, characterized in that (a) in a first reaction step cyanurchloride is reacted with the disodium salt of 4,4'-diaminostilbene-2,2'-disulfonic acid to give the intermediate of formula (2); (b) in a second reaction step the compound of formula (2) is reacted with a compound of formula $R_1$—H and/or $R_2$—H to give the compound of formula (3); (c) in a third step the compound of formula (3) is reacted with the compound of the formula $R_3H$, and reaction step (a) and/or (c) are carried out in a medium consisting of a mixture of water and a polyglycol to give the compound of formula (1), wherein $R_1$, $R_2$ and $R_3$, independently, are phenylamino; phenylamino substitued by $C_1$–$C_3$alkyl, halogen, cyano, COOR or COR; CONH—R; $SO_2NH$—R; NH—COR; mono- or disulphonated phenylamino; morpholino; piperidino; pyrrolidino; —$NH_2$; —$NH(C_1$-$C_4$alkyl); —$N(C_1$–$C_4$alkyl)$_2$; —$NH(C_2$–$C_4$hydroxyalkyl); —$N(C_2$–$C_4$hydroxyalkyl)$_2$; —$N(C_1$–$C_4$alkyl)($C_2$–$C_4$hydroxyalkyl); $NHC_2$–$C_4$ alkylsulphonic acid; —$OC_1$–$C_4$alkyl; an aminoacid or aminoacid amide residue from which a hydrogen atom on the amino group has been removed; $R_1$ and $R_2$ may further independently represent hydrogen; $C_1$–$C_4$alkyl; phenyl; naphthyl; phenyl or naphthyl substituted by $C_1$–$C_4$alkyl, $C_1$–$C_4$alkoxy, halogen, $C_2$–$C_5$alkanoyl-amino, nitro, sulpho or $C_1$–$C_4$alkylated amino; R is hydrogen; or $C_1$–$C_3$alkyl; and M is H, Na, Li, K, Ca, Mg, ammonium, or ammonium that is mono-, di-, tri- or tetrasubstituted by $C_1$–$C_4$alkyl, $C_2$–$C_4$hydroxyalkyl or a mixture thereof.

10 Claims, No Drawings

PROCESS FOR THE PREPARATION OF STILBENE COMPOUNDS

The present invention relates to a new process for the preparation of 4,4'-bis-(triazinyl-amino)-stilbene-2,2'-disulphonic acid compounds and compositions containing them.

The preparation of 4,4'-bis-(triazinylamino)-stilbene-2,2'-disulphonic acid derivatives by primarily reacting 4,4-diaminostilbene-2,2'-disulphonic acid with cyanuric chloride and successively replacing the remaining chlorine atoms by nucleophiles has long been known (see, for example: "Fluorescent Whitening Agents", R. Anliker and G. Müller, G. Thieme Publishers,1975, p.31 ff.), as has the use of such compounds as fluorescent whitening agents. However, as reported in the above citation, undesirable byproducts may often be formed, especially during the final reaction step (i.e. replacement of the third chlorine atom of cyanuric chloride), in which higher temperatures, longer reaction times, increased pressure and, possibly, excess of amines are required.

Surprisingly, it has now been found that this reaction step can be carried out more efficiently if the reaction is performed in a medium consisting of a of water and polyglycol mixture. A further advantage of this procedure is that the resulting reaction mixture is a stable formulation of the fluorescent whitening agent which, if required, may be directly utilised without intermediate isolation.

Correspondingly, the subject of the present invention is a process for the preparation of a 4,4'-bis-(triazinylamino)-stilbene-2,2'-disulphonic acid of the formula (1)

characterised in that
(a) in a first reaction step cyanurchloride is reacted with the disodium salt of 4,4'-diaminostilbene-2,2'-disulfonic acid to give the intermediate of the formula (2)

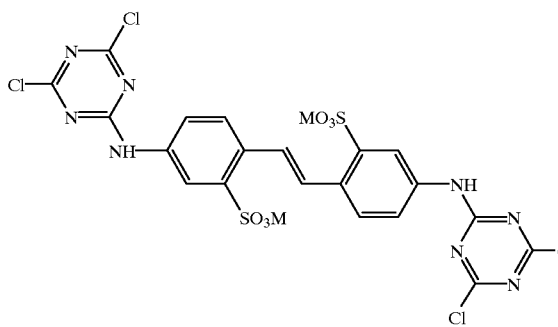

(b) in a second reaction step the compound of formula (2) is reacted with a compound of formula $R_1$—H and/or $R_2$—H to give the compound of the formula (3)

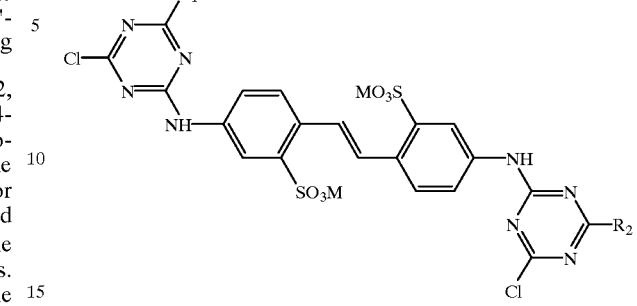

(c) in a third step the compound of formula (3) is reacted with the compound of the formula $R_3H$, and reaction step (a) and/or (c) are carried out in a medium consisting of a mixture of water and a polyglycol to give the compound of formula (1), wherein
$R_1$, $R_2$ and $R_3$, independently, are phenylamino; phenylamino substituted by $C_1$–$C_3$alkyl, halogen, cyano, COOR or COR; CONH—R; $SO_2NH$—R; NH—COR; mono- or disulphonated phenylamino; morpholino; piperidino; pyrrolidino; —$NH_2$; —NH($C_1$–$C_4$alkyl); —N($C_1$–$C_4$alkyl)$_2$; —NH($C_2$–$C_4$hydroxyalkyl); —N($C_2$–$C_4$hydroxyalkyl)$_2$; —N($C_1$–$C_4$alkyl)($C_2$–$C_4$hydroxyalkyl); $NHC_2$–$C_4$ alkylsulphonic acid; —$OC_1$–$C_4$alkyl; an aminoacid or aminoacid amide or a polyethyleneglycol residue from which a hydrogen atom on the amino group has been removed; or a polyethyleneglycol from which a hydrogen atom of the —OH-group was removed;
$R_1$ and $R_2$ may further independently represent hydrogen; $C_1$–$C_4$alkyl; phenyl; naphthyl; phenyl or naphthyl substituted by $C_1$–$C_4$alkyl, $C_1$–$C_4$alkoxy, halogen, $C_2$–$C_5$alkanoylamino, nitro, sulpho or $C_1$–$C_4$alkylated amino;
R is hydrogen; or $C_1$–$C_3$alkyl; and
M is H, Na, Li, K, Ca, Mg, ammonium, or ammonium that is mono-, di-, tri- or tetrasubstituted by $C_1$–$C_4$alkyl, $C_2$–$C_4$hydroxyalkyl or a mixture thereof.

Compounds of formula (1) in which M is H, Li, K, Ca, Mg, ammonium, or ammonium that is mono-, di-, tri- or tetrasubstituted by $C_1$–$C_4$alkyl, $C_2$–$C_4$hydroxyalkyl or a mixture thereof can be readily prepared from corresponding compounds of formula (1) in which M is Na by methods known per se, for example those disclosed in U.S. Pat. Nos. 4,737,240 and 5,288,294.

The final product of formula (1) can comprise 1 to 20%, preferably 1 to 10% b.w. of components wherein $R_3$ is a polyethyleneglycol from which a hydrogen atom of the —OH-group was removed.

As $C_1$–$C_4$alkyl, there are defined methyl, ethyl, n-propyl, isopropyl, n-butyl, sec-butyl or tert-butyl.

The reactants are generally used in substantially the stoichometric proportions required to form the compounds of formula (1).

The polyglycol preferably has a molecular weight within the range of about 200 to 5000 and is more preferably a polyethyleneglycol of molecular weight of about 200 to 1500.

Further polyglycols that can be use for the present process are block copolymers of ethylene oxide and propylene oxide which may be represented by the formula

wherein a is from 0.5 to 230; and b is form 15 and 80.

These block copolymers are also suitable for different paper, textile, detergent and cosmetic applications.

The ratios of polyglycol to water, which may be used in the above process for the first and/or third reaction step, can lie between 90:10 and 10:90, but preferably lie within the range of 30:70 to 70:30.

The temperature at which the reaction is carried out may lie between 50° C. and the boiling point of the polyglycol-water mixture, but is preferably at the boiling point of the mixture.

The reaction may be carried out at a pH value of between 7.5 and 12.5, but is preferably performed at between pH 8.5 and 9.0.

The process is particularly suitable for the preparation of a compound of formula

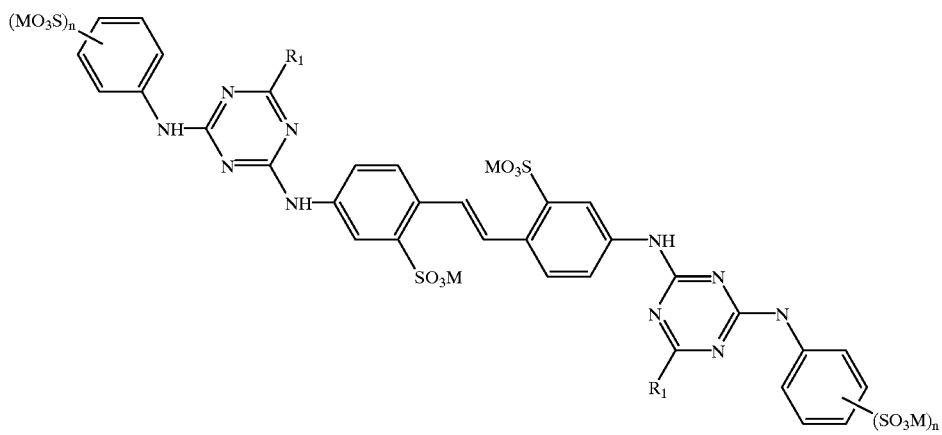

wherein M and $R_1$ are as defined in claim 1 and n is 0, 1 or 2.

Especially preferred compounds are those of formula (4) in which each M is hydrogen, sodium or potassium and, furthermore, those in which $R_1$ represents morpholino, —$NH_2$; N—($CH_2$—$CH_3$)$_2$; —$NHCH_3$; —N($CH_3$)$CH_2CH_2OH$; $NHCH_2CH_2OH$, —N($CH_2CH_2OH$)$_2$, —N($CH_3$)($CH_2CH_2OH$) or —$NHCH_2CH_2SO_3H$ and also those in which $R_1$ represents an amino acid residue from which a hydrogen atom on the amino group has been removed. Specific examples of aminoacids from which such preferred aminoacid residues $R_1$ are derived include glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid and taurine, as well as mixtures and optical isomers thereof. Of these aminoacids from which such preferred aminoacid residues $R_1$ are derived, sarcosine, taurine, glutamic acid and aspartic acid are particularly preferred.

In the final reaction step a reaction mixture of the compound of formula (1) and the corresponding polyglycol/water mixture is obtained. A further advantage of the present invention is that this mixture comprising polyglycol which has multi-functional properties as mentioned above can directly be used without further treatment for paper, textile, detergent and cosmetic applications.

An other aspect of the present invention is therefore a liquid composition containing the compounds of formula (1) in a polyglycol-water mixture.

Preferably the liquid composition contains 5 to 40% of compounds of formula (1) and 95 to 60% of a polyglycol-water mixture, whereby the ratio of polyglycol to water lies between 90:10 and 10:90 parts by weight.

In dissolved or finely divided states, the brighteners obtained by the above process display a more or less pronounced fluorescence. They are therefore used, according to the invention, for optically brightening synthetic or natural organic materials.

Examples of such materials which may be mentioned, without the review given below being intended to express any limitation thereto, are textile fibres from the following groups of organic materials, insofar as optical brightening thereof enters into consideration:

(a) Polyamides which are obtainable as polymerisation products by ring opening, for example those of the polycaprolactam type, (b) polyamides which are obtainable as polycondensation products based on bifunctional or polyfunctional compounds capable of undergoing a condensation reaction, such as hexamethylenediamine adipate and (c) natural textile organic materials of animal or vegetable origin, for example based on cellulose or proteins, such as cotton or wool, linen or silk.

The organic materials to be optically brightened can be in diverse stages of processing and are preferably finished textile products. They can, for example be in the form of hank goods, textile filaments, yarns, twisted yarns, nonwovens, felts, textile fabrics, textile composites or knitted fabrics.

The brighteners defined above are of particular importance for the treatment of textile fabrics. The treatment of textile substrates is advantageously carried out in an aqueous medium in which the particular optical brighteners are present in a finely divided form (suspensions, so-called microdispersions and in some cases solutions). Dispersing agents, stabilisers, wetting agents and further auxiliaries can optionally be added during the treatment.

The treatment is usually carried out at temperatures of from about 20° to 140° C., for example at the boiling point of the bath, or in the region thereof (about 90° C.). For the finishing, according to the invention, of textile substrates it is also possible to use solutions or emulsions in organic solvents, as are used in dyeing practice in so-called solvent dyeing (pad-thermofix method and the exhaustion dyeing process in dyeing machines).

The optical brighteners which can be used according to the present invention can also be employed, for example, in the following use forms:

(a) In mixtures with so-called "carriers", wetting agents, softeners, swelling agents, antioxidants, light stabilisers, heat stabilisers and chemical bleaching agents (chlorite bleach and bleaching bath additives).

(b) In mixtures with crosslinking agents and finishing agents (for example starch or synthetic finishing agents) and also in combination with very diverse textile finishing processes, especially synthetic resin finishes (for example crease resistant finishes such as "wash-and-wear", "permanent press" and "no-iron"), and also flame resistant finishes, soft handle finishes, anti-soiling finshes or anti-static finishes or antimicrobial finishes.

(c) As additives to various soaps and washing agents.

(d) In combination with other substances having an optical brightening action.

If the brightening process is combined with textile treatment or finishing methods, the combined treatment can in many cases advantageously be effected with the aid of corresponding stable formulations which contain the compounds having an optical brightening action in a concentration such that the desired brightening effect is obtained.

In certain cases, the full effect of the brightener is achieved by an after-treatment. This can be, for example, a chemical treatment (for example acid treatment), a thermal treatment (for example heat) or a combined chemical/heat treatment.

The amount of the optical brighteners to be used according to the invention, relative to the material to be optically brightened, can vary within wide limits. A distinct and durable effect can already be achieved with vary small amounts and in certain cases, for example, with amounts of 0.03% by weight. However amounts of up to about 0.5% by weight can also be used. For most cases of interest in practice, amounts of between 0.05 and 0.5% by weight relative to the material to be brightened, are preferably of interest.

The optical brighteners are also especially suitable as additives for washing baths or to industrial and household washing agents and they can be added in various ways. They are appropriately added to washing baths in the form of their solutions in water or organic solvents or also in a state of fine division as aqueous dispersions or slurries. They, or their components, are advantageously added to household or industrial washing agents at any phase of the manufacturing process of the washing agent, for example to the so-called "slurry" prior to spray-drying of the washing powder or during the preparation of liquid washing agent combinations. The compounds can be added both in the form of a solution or dispersion in water or other solvents and also without auxiliaries in the form of a dry brightener powder. However, they can also be sprayed, in the dissolved or pre-dispersed form, onto the finished washing agent.

Washing agents which can be used are the known mixtures of detergent substances, such as, for example, soap in the form of chips and powders, synthetic products, soluble salts of sulphonic acid half-esters of higher fatty alcohols, arylsulphonic acids, which are substituted by higher alkyl and/or polysubstituted by alkyl, carboxylic acid esters with alcohols of medium to higher molecular weight, fatty acid acylaminoalkyl- or aminoaryl-glycerol-sulphonates, phosphoric acid esters of fatty alcohols and the like. So-called "builders" which can be used are, for example, alkali metal polyphosphates and alkali metal polymeta-phosphates, alkali metal pyrophosphates, alkali metal salts of carboxyethylcellulose and other "soil redeposition inhibitors", and also alkali metal silicates, alkali metal carbonates, alkali metal borates, alkali metal perborates, nitrilotriacetic acid, ethylenediamine-tetraacetic acid and foam stabilisers, such as alkanolamides of higher fatty acids. Furthermore, the washing agents can contain, for example: antistatic agents, superfatting skin protection agents, such as lanolin, enzymes, antimicrobial agents, perfumes and dyestuffs.

The brighteners have the particular advantage that they are also effective in the presence of active chlorine donors, such as, for example, hypochlorite and can be used without substantial loss of the effects in washing baths with non-ionic washing agents, for example alkylphenol polyglycol ethers. Also in the presence of perborate or peracids and activators, for example tetraacetylglycoluril or ethylenediamine-tetraacetic acid are the new brighteners very stable both in pulverulent washing agent and in washing baths.

The brighteners according to the invention are added in amounts of 0.005 to 2% or more and preferably of 0.03 to 0.5%, relative to the weight of the liquid or pulverulent ready-to-use washing agent. When they are used to wash textiles made of cellulose fibres, polyamide fibres, cellulose fibres with a high grade finish, wool and the like, wash liquors which contain the indicated amounts of the optical brighteners according to the invention impart a brilliant appearance in daylight.

The washing treatment is carried out, for example, as follows: The indicated textiles are treated for 1 to 30 minutes at 5° C. to 100° C. and preferably at 25° to 100° C. in a wash bath which contains 1 to 10 g/kg of a composite washing agent containing builders and 0.05 to 1% relative to the weight of the washing agent, of the brighteners claimed. The liquor ratio can be 1:3 to 1:50. After washing, the textiles are rinsed and dried in the customary manner. The wash bath can contain, as a bleach additive, 0.2 g/l of active chlorine (for example in the form of hypochlorite) or 0.1 to 2 g/l of sodium perborate. The brighteners according to the invention can also be applied from a rinsing bath with a "carrier". For this purpose the brightener is incorporated in a soft rinsing agent or in another rinsing agent, which contains, as the "carrier", for example, polyvinyl alcohol, starch, copolymers on an acrylic basis or formaldehyde/urea or ethylene-urea or propylene-urea derivatives, in amounts of 0.005 to 5% or more and preferably of 0.2 to 2%, relative to the rinsing agent. When used in amounts of 1 to 100 ml, and preferably of 2 to 25 ml, per liter of rinsing bath, rinsing agents of this type, which contain the brighteners according to the invention, impart brilliant brightening effects to very diverse types of treated textiles.

A further application of the compounds of the invention is for the brightening of paper, either in the pulp mass during paper manufacture or in the size-press, which has been described in British Patent Specification 1,247,934, or preferably in coating compositions. When brighteners of the present invention are employed in such formulations papers brightened with them exhibit a very high degree of whiteness.

In certain cases the compounds obtained by the process of the present invention may be useful as ultraviolet absorbing agents (UVAs) and, as such, are useful for improving the sun protection factor (SPF) of textile fibre materials, as described, for example, in European Patent Application 728749.

The following Example serves to illustrate the invention; parts and percentages are by weight, unless otherwise stated.

EXAMPLE 1

38 g of the compound of formula

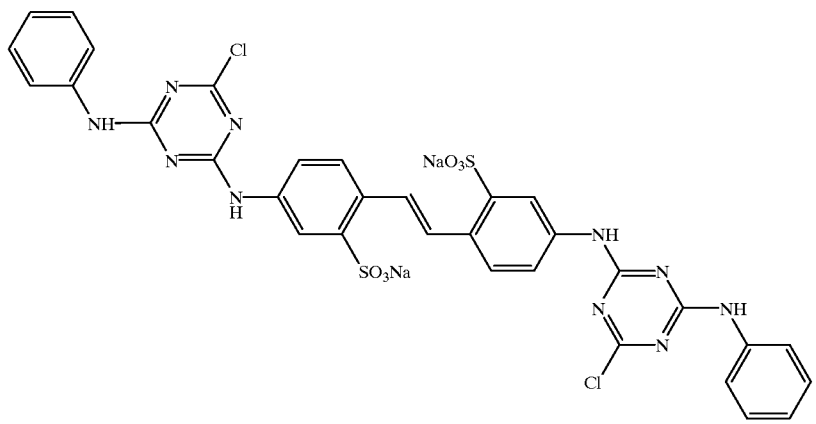
(101)

are suspended in 38 g of polyethyleneglycol-600 and 30 g of water. A solution of 17.16 g of the disodium salt of aspartic acid in 23 g of water is then added. The reaction mixture is then heated under reflux at 95° C. with stirring for 6 hours, whilst maintaining the pH at 8.5 to 9.0 by the addition of 11.5 g of 32% sodium hydroxide solution.

The resulting solution contains the compound of formula in a yield of 96%.

The resulting solution is stable for a period of at least 1 month at −5° C. and consists of:

Compound of the formula (102): 28%
Water: 45%
Polyethyleneglycol: 22%
Sodium chloride: 3%

This solution may be used directly for the optical brightening of textiles, detergents and paper or for improving the sun protection factor of textile fibre material.

If desired, the product may be obtained as yellowish crystals, free from polyethyleneglycol, by precipitation with warm ethanol.

Analogous results can also be obtained by the use of polyethyleneglycol 300 or 1500.

EXAMPLE 2

1 kg (0.9 mMol) of the wet compound of the formula (101) are suspended in a solution of 159 g (1.71 mol) aniline in 2.5 kg polyethylenglycol-300 and stirred under reflux condition at 130° C. for 30 minutes. First a clear solution

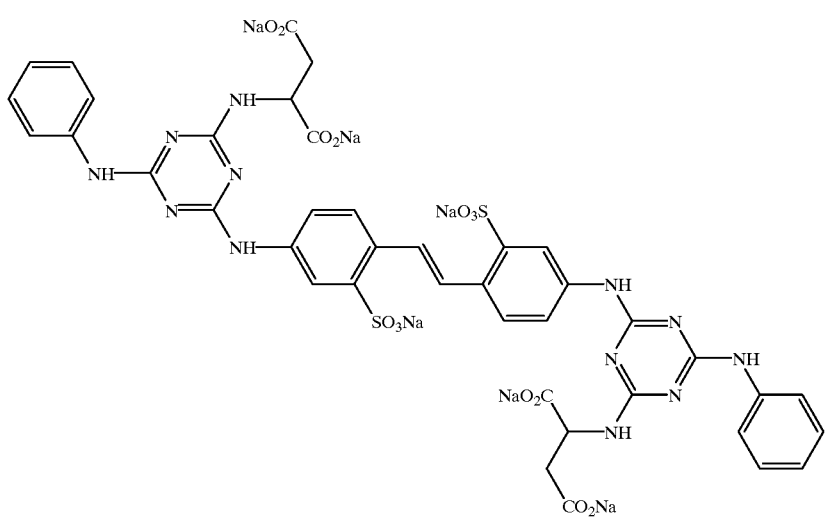
(102)

results and then the free acid of TAS precipitates. After cooling down the free acid is filtered by suction and washed with water.

In another variation 225 g of hot NaOH (32%) and 275 g of water is added to the reaction mixture. After cooling down 4 kg of a clear 23.4% solution of the compound of formula (103)

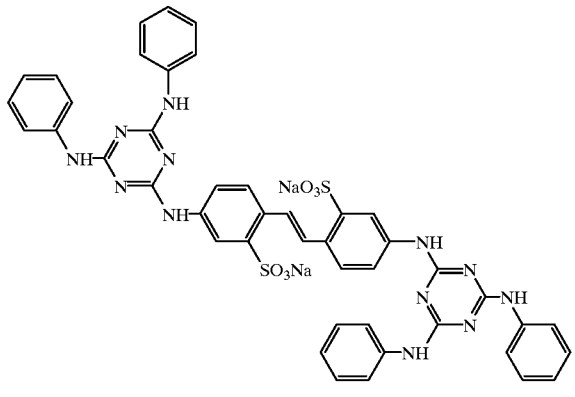

are obtained.

EXAMPLE 3

120 g (0.65 mol) of cyanurchloride are suspended in a mixture of 250 g polyethyleneglycolether-300 and 300 g ice water. 1057 g (0.314 mol) of a 12% solution of 4,4'-diaminostilbene-2,2'-disulfonic acid in water are added. The pH is controlled by the addition of sodium carbonate (20%). The reaction mixture is warmed up to 30° C., the pH is fixed to 7 with sodium carbonate (20%) and 61.3 g (0.659 mol) of aniline is added. The reaction mixture is warmed up to 80° C. and the pH is controlled by NaOH (50%). Stirring is continued for 30 minutes at 80° C. and pH 7. The mixture is heated to 96° C. and 81.6 g (0.82 mol) diethanolamine is added at pH 8.2–8.5. A two-phase reaction mixture is obtained.

After 30 minutes 150 ml of a concentrated NaCl solution are added. The organic phase is separated and diluted with 200 g polyethyleneglycol-300 and 15 g water. The pH is adjusted to 10 with 4 g of NaOH (50%) and the mixture is filtered.

The reaction formulation has a content of 24.8% of the compound of formula (104)

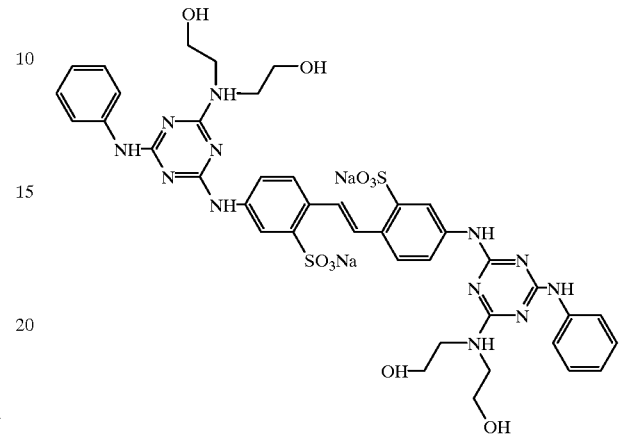

which has a clear aspect even after a storage time of one month.

The compound which is free of solvents can be isolated by precipitating in ethanol.

Yield: 89% with respect to 4,4'-diaminostilbene-2,2'-disulfonic acid.

EXAMPLE 4

10.4 g of the compound of formula (105)

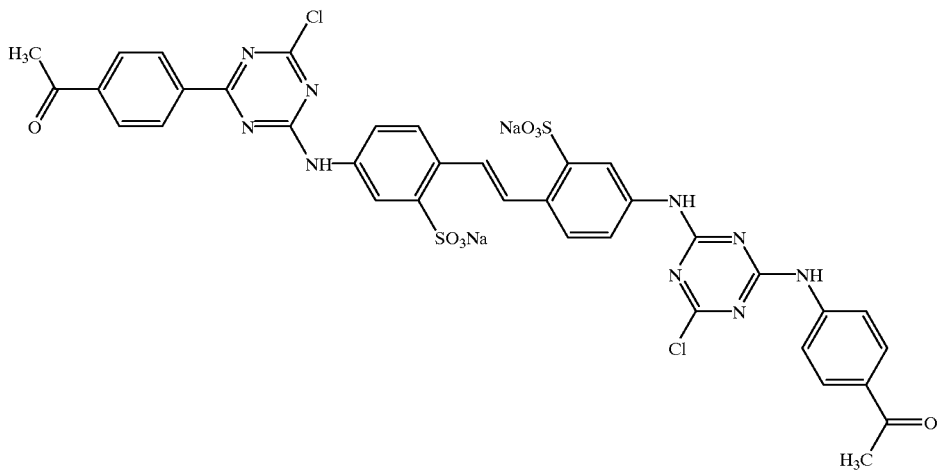

are suspended in 41 g polyethyleneglycol 200 and 14 g butyltriglycol. To this mixture a solution of 3.1 g (23 mMol) of aspartic acid in 12 ml water and 2.66 g NaoH (30%) are added. The reaction mixture is warmed to 90° C. and the pH is adjusted to 8.5 to 9 with NaCOH (30%). After 5 h a slightly opaque solution is obtained and the pH of this solution remains stable. After cooling down and filtering a stable clear reaction formulation of the compound formula

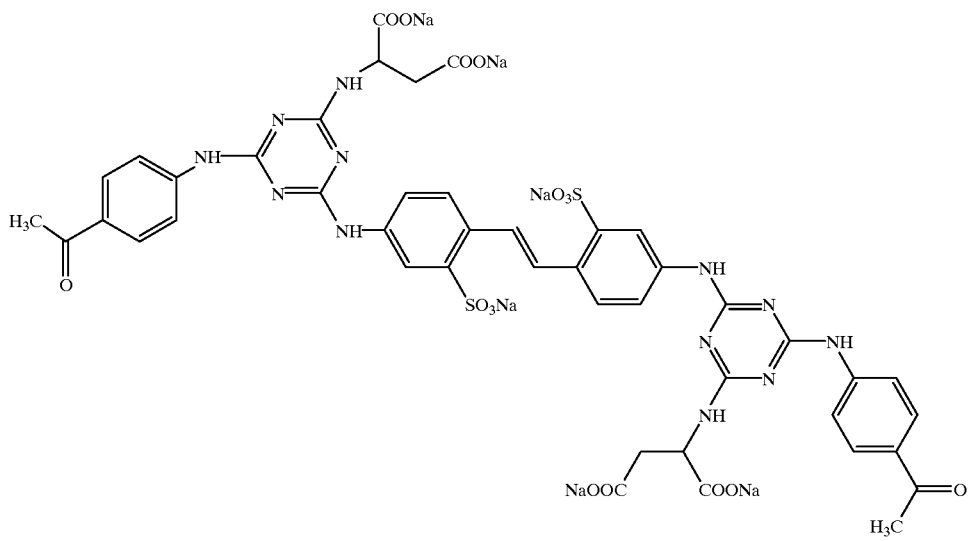

(106)

Yield: 95%; Content: 14%.

The compound can by isolated by precipitating in acetone/HCl followed by converting in the hexa-sodiumsalt.

Elemental analysis for $C_{44}H_{34}N_{12}Na_6O_{16}S_2$, +NaCl and 14.4 $H_2O$:

|  | C | H | N | S |
|---|---|---|---|---|
| Requested: | 35.1 | 4.28 | 11.16 | 4.26 |
| Found: | 35.0 | 4.3 | 11.2 | 4.4 |

EXAMPLE 5

38 g (66%=30.4 mmol) of the of the wet compound of the formula (101) are submitted in 40 g water and 12 g polyethyleneglycol-300. 5.42 g (70 mmol) methylamine (40% solution in water) are added and warmed up to 90° C. At this temperature the mixture is stirred for 5 h and the pH is fixed at 8,5 adding NaOH 30%. At the end of the reaction the pH remains constant. The mixture is cooled down to room temperature. A clear reaction formulation comprising 16% of the compound of formula is obtained after addition of 38 g of polyethyleneglycol-300 to the two-phase reaction mixture.

Identification and content is proved via HPLC and trade product (Blankophor HRS).

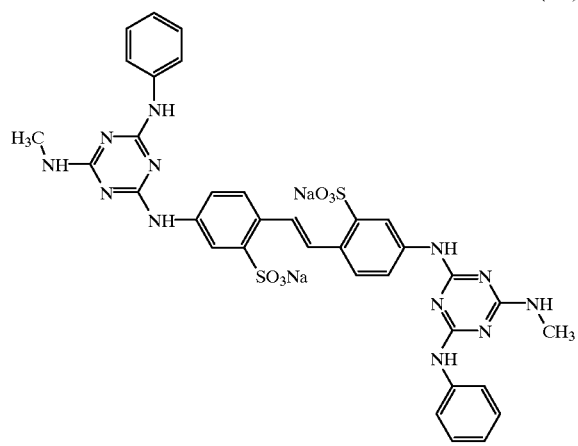

(107)

What is claimed is:
1. A process for the preparation of a 4,4'-bis-(triazinylamino)-stilbene-2,2'-disulphonic acid of the formula

(1)

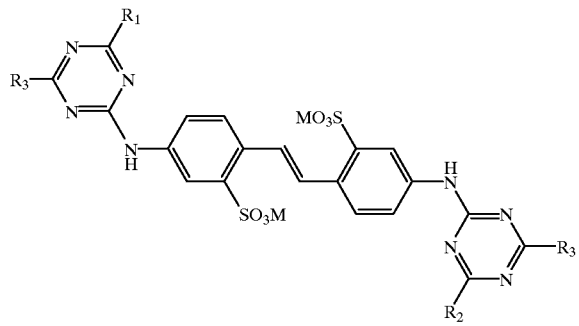

characterised in that (a) in a first reaction step cyanuric chloride is reacted with the disodium salt of 4,4'-diaminostilbene-2,2'-disulfonic acid to give the intermediate of the formula (2)

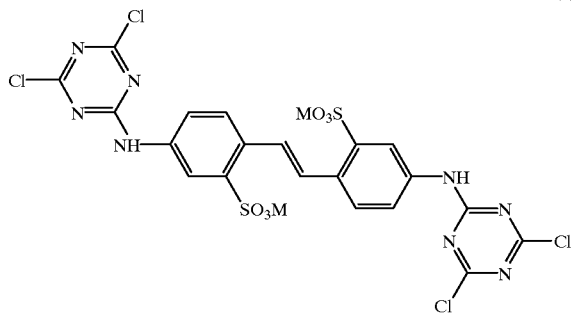

(b) in a second reaction step the compound of formula (2) is reacted with a compound of formula $R_1H$ and/or $R_2$—H to give the compound of the formula (3)

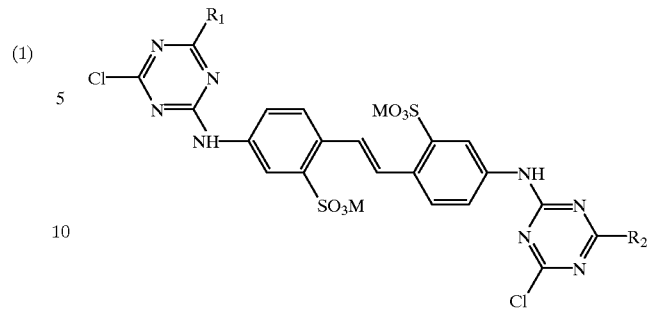

(c) in a third step the compound of formula (3) is reacted with the compound of the formula $R_3H$, and reaction step (a) and/or (c) are carried out in a medium consisting of a mixture of water and a polyglycol to give the compound of formula (1), wherein $R_1$, $R_2$ and $R_3$, independently, are phenylamino; phenylamino substituted by $C_1$–$C_3$alkyl, halogen, cyano, COOR or COR; CONH—R; $SO_2$NH—R; NH—COR; mono- or disulphonated phenylamino; morpholino; piperidino; pyrrolidino; —$NH_2$; —NH($C_1$–$C_4$alkyl); —N($C_1$–$C_4$alkyl)$_2$; —NH($C_2$C$_4$hydroxyalkyl); —N($C_2$–$C_4$hydroxyalkyl)$_2$; —N($C_1$–$C_4$alkyl)($C_2$–$C_4$hydroxyalkyl); —NH$C_2$–$C_4$alkylsulphonic acid; —$OC_1$–$C_4$alkyl; an aminoacid or aminoacid amide residue from which a hydrogen atom on the amino group has been removed; or a polyethylene glycol from which a hydrogen atom of the —OH-group was removed;

R is hydrogen; or $C_1$–$C_3$alkyl; and

M is Na.

2. A process according to claim 1 wherein the reactants are used in substantially the stoichometric proportions required to form the compounds of formula (1).

3. A process according to claim 1 in which the polyglycol is of molecular weight in the range 200 to 5000.

4. A process according to claim 1 in which the ratio of polyglycol to water lies between 90:10 and 10:90 parts by weight.

5. A process according to claim 1 in which the reaction is carried out at a temperature of between 50° C. and the boiling point of the polyglycol-water mixture.

6. A process according to claim 1 in which the reaction is carried out at a pH value within the range 7.5 to 12.5.

7. A process according to claim 1 for the preparation of a compound of formula (4)

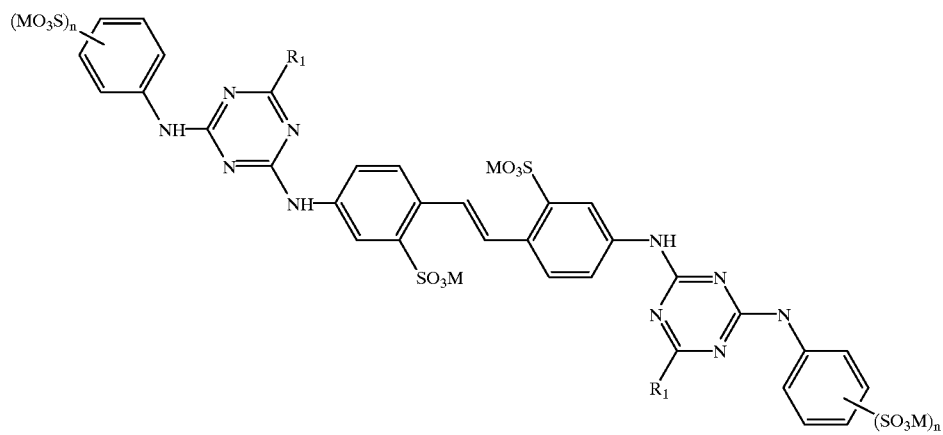

wherein M and $R_1$ are as defined in claim 1 and n is 0, 1 or 2.

8. A process according to claim 7 in which $R_1$ represents morpholino, $-NH_2$; $N-(CH_2-CH_3)_2$; $-NHCH_3$; $-N(CH_3)CH_2CH_2OH$; $NHCH_2CH_2OH$, $-N(CH_2CH_2OH)_2$, $-N(CH_3)(CH_2CH_2OH)$ or $-NHCH_2CH_2SO_3H$.

9. A process according to claim 7 in which $R_1$ represents an amino acid residue from which a hydrogen atom on the amino group has been removed.

10. A process according to claim 9 in which the amino acid residue is derived from aspartic acid, glutaric acid, sarcosine or taurine.

* * * * *